US00PP31082P3

(12) United States Plant Patent
de Jongh

(10) Patent No.: US PP31,082 P3
(45) Date of Patent: Nov. 19, 2019

(54) ***FRAGARIA* PLANT NAMED 'BLOSSOMBERRY'**

(50) Latin Name: ***Fragaria* x *ananassa***
Varietal Denomination: Blossomberry

(71) Applicant: Beekers Berries Breeding B. V., Breda (NL)

(72) Inventor: Johannes Adrianus Petrus de Jongh, Etten-Leur (NL)

(73) Assignee: BEEKERS BERRIES BREEDING BV, Breda (NL)

( * ) Notice: Subject to any disclaimer, the term of this patent is extended or adjusted under 35 U.S.C. 154(b) by 0 days.

(21) Appl. No.: 16/350,042

(22) Filed: Sep. 17, 2018

(65) Prior Publication Data

US 2019/0090397 P1 Mar. 21, 2019

(30) Foreign Application Priority Data

Sep. 18, 2017 (QZ) ..... PBR 2017/2248

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./156, 208
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new and distinct cultivar of *Fragaria* plant 'Blossomberry' characterized by its white berries with red achenes with the sun exposed side of the berries flushed with pink, its firm berries, its flowers that produce pollen, its berries with a fruit weight of 10 to 20 grams, and its berries that are produced in June in The Netherlands.

3 Drawing Sheets

Botanical classification: *Fragaria* x *ananassa.*
Variety denomination: 'Blossomberry'.

CROSS REFERENCE TO A RELATED APPLICATION

This application is related to U.S. Plant Patent for a plant derived from the same breeding program that is entitled *Fragaria* Plant Named 'BBB PO 01' (U.S. Plant Pat. No. 24,332).

BACKGROUND OF THE INVENTION

The present invention includes a new and distinct cultivar of *Fragaria* x *ananassa* named 'Blossomberry', and will herein be referred to as 'Blossomberry'. The new cultivar is a new pineberry grown for fresh fruit production.

The new variety resulted from an ongoing breeding program by the Inventor in Etten-Leur, The Netherlands. The objectives of the breeding program were to improved cultivars of strawberries with white fruit and particularly that produce pollen and exhibit firmer fruit.

'Blossomberry' arose from a cross between *Fragaria* 'BBBPO 02' (not patented) as the female parent and an unnamed proprietary plant from the breeders breeding program, designated as 14-132, as the male parent in March 2015. The new cultivar was selected in May 2016 as a single unique plant amongst the resulting seedlings from the above cross.

Asexual reproduction of the new cultivar was first accomplished by stem cuttings by the Inventor in July 2016 in Etten-Leur, The Netherlands. Asexual reproduction by stem cutting and tissue culture using meristematic tissue has shown that the unique characteristics of 'Blossomberry' are stable and reproduced true to type in successive generations.

BRIEF SUMMARY OF THE INVENTION

The following traits have been repeatedly observed and represent the characteristics of the new *Fragaria*. These attributes in combination distinguish 'Blossomberry' as unique and distinct from all other cultivars of *Fragaria* known to the Inventor.

1. 'Blossomberry' exhibits white berries with red achenes with the sun exposed side of the berries flushed with pink.
2. 'Blossomberry' exhibits firm berries.
3. 'Blossomberry' exhibits flowers that produce pollen.
4. 'Blossomberry' exhibits berries with a fruit weight of 10 to 20 grams.
5. 'Blossomberry' exhibits berries that are produced in June in The Netherlands.

The female parent of 'Blossomberry' is similar to BBB A01' in having whitish fruit but differs from 'Blossomberry' in having flowers that do not produce pollen, in having fruit that is smaller, less firm, and lacks a pink blush with sun exposure, and in having less fruit production. The male parent of 'Blossomberry' is similar to BBB A01' in fruit shape and in having flowers that produce pollen, but differs from 'Blossomberry' in having red fruit that is larger in size. 'Blossomberry ' can also be compared to the *Fragaria* cultivar 'BBB PO 01' (U.S. Plant Pat. No. 24,332). 'BBB PO 01' is similar to 'Blossomberry' in having fruit with whitish in color with white flesh. 'BBB PO 01' differs from BBB A01' in fruit that is softer, much smaller in size, in producing many more runners, and in having flowers that does not produce pollen.

BRIEF DESCRIPTION OF THE DRAWING

The accompanying color photographs depict the characteristics of 'Blossomberry' of plants about one year in age from propagation of as grown in an unheated greenhouse in a 4-liter container in Etten-Leur, The Netherlands. The colors in the photographs are as close as possible with the digital photography and printing techniques utilized and the color codes in the detailed botanical description accurately describe the colors of the new *Fragaria*.

The photograph in FIG. 1 provides a view of a typical plant of 'Blossomberry' in various stages fruit production.

Figure 1:
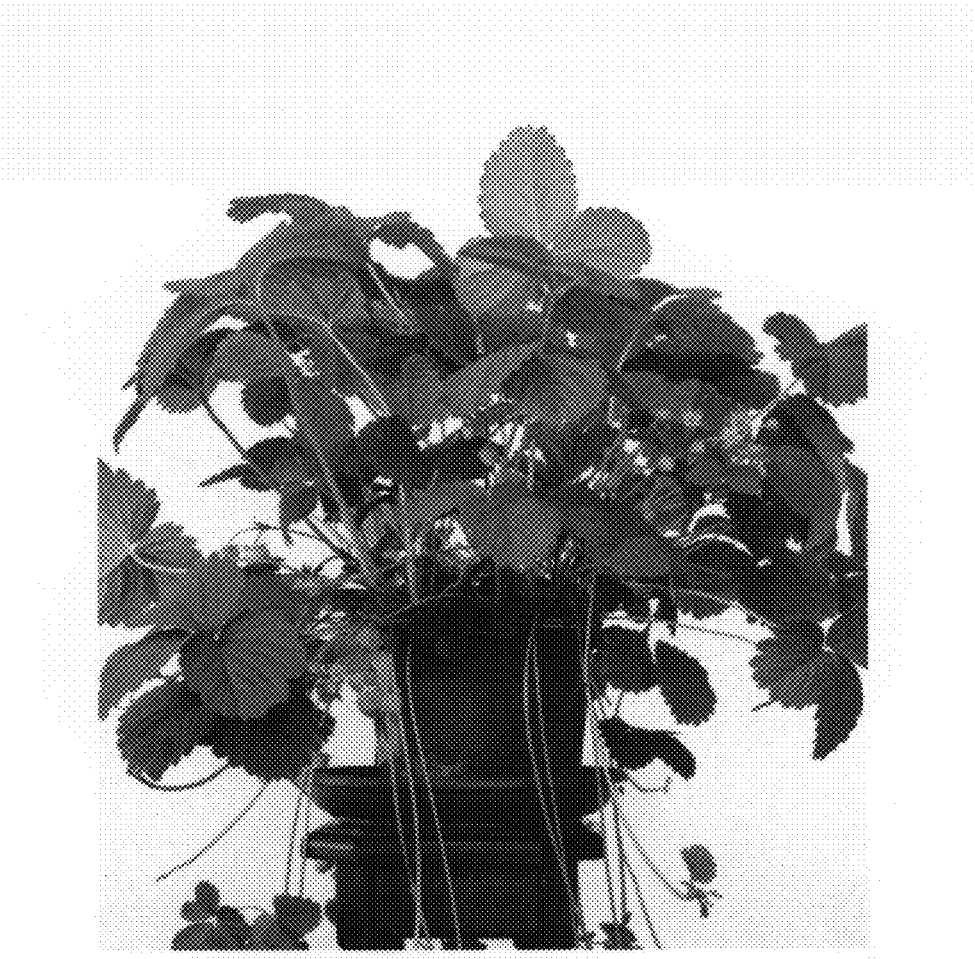
Figure 2:
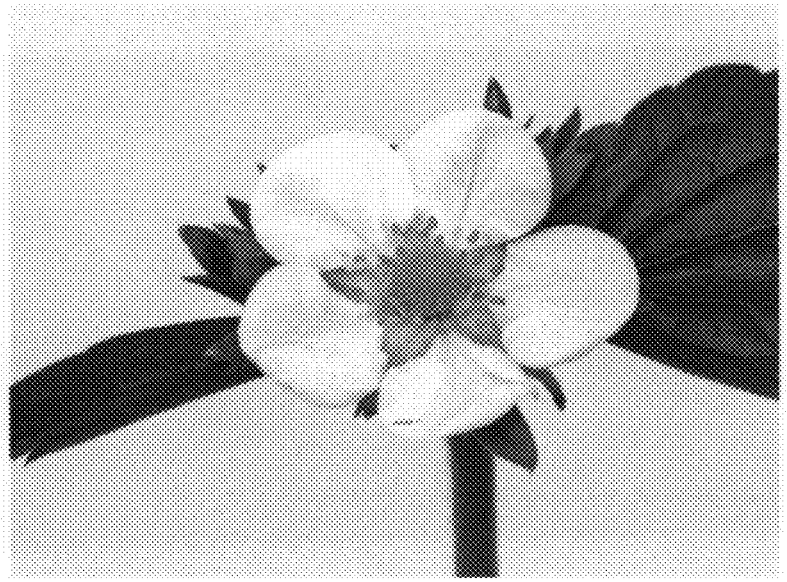

The photograph in FIG. 2 provides a close-up of a flower of 'Blossomberry'.

Figure 3:
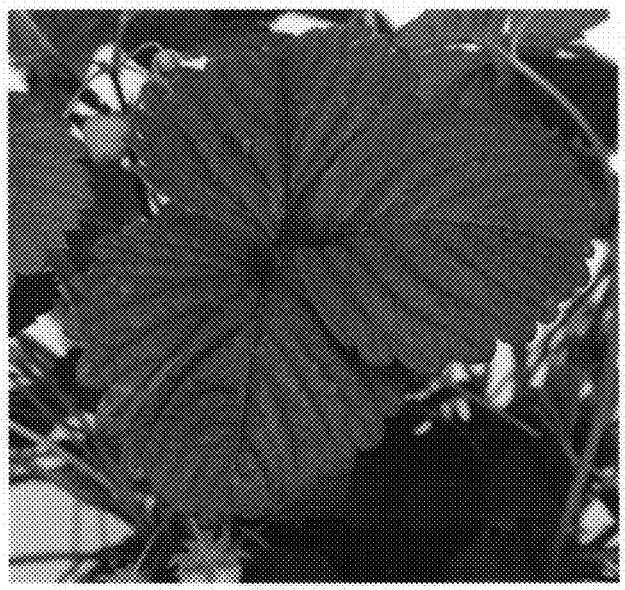

The photograph in FIG. 3 provides a close-up view of a leaf of 'Blossomberry'.

Figure 4:
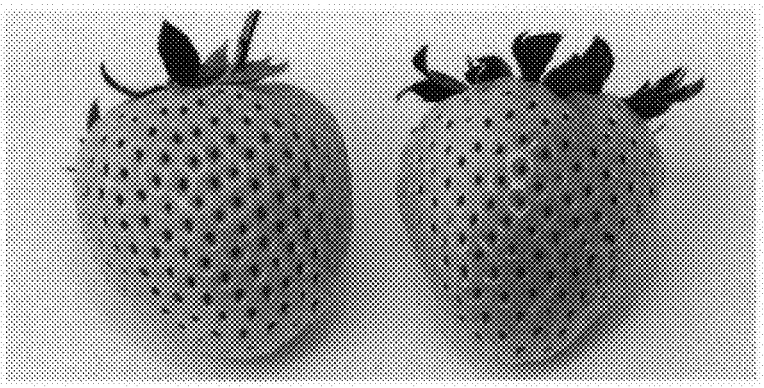

The photograph in FIG. 4 provides a close-up of the sun exposed side of the fruit of 'Blossomberry'.

Figure 5:
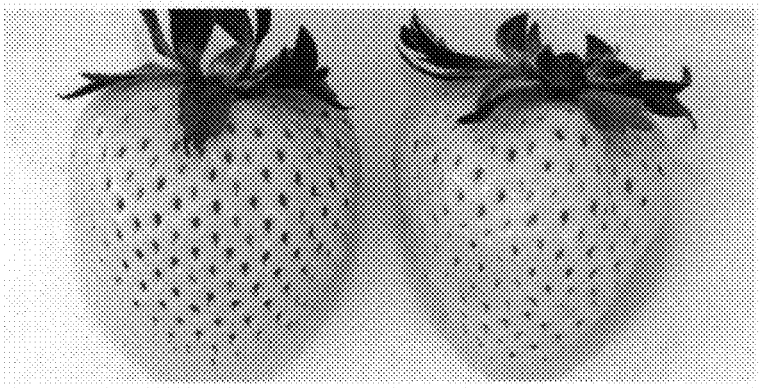

The photograph in FIG. 5 provides a close-up of the shaded side of the fruit of 'Blossomberry'.

Figure 6:
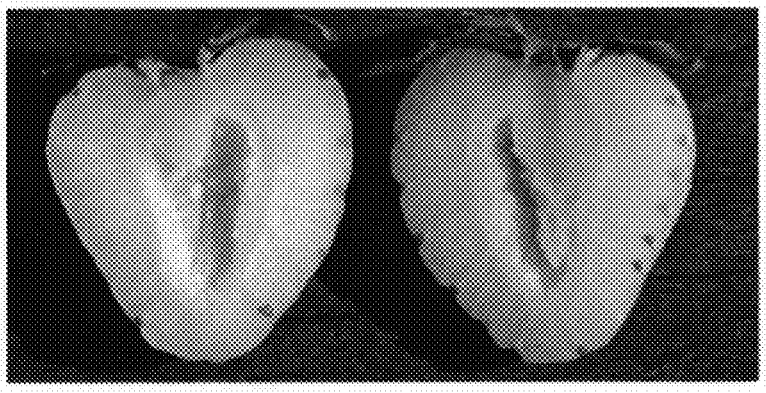

The photograph in FIG. 6 provides a close-up view of the fruit flesh of 'Blossomberry'.

DETAILED BOTANICAL DESCRIPTION

The following is a detailed description of plants 9 months in age as grown in an unheated greenhouse in 19-cm containers (4 plugs per container) in Made, the Netherlands. The characteristics may vary in detail depending on variations in conditions such as temperature, day-length, light intensity, soil types, and water and fertility levels as 'Blossomberry ' was not tested under all possible environmental conditions. The color determination is in accordance with The 2015 Colour Chart of The Royal Horticultural Society, London, England, except where general color terms of ordinary dictionary significance are used.

General description:

*Plant type*.—Herbaceous perennial.

*Plant habit*.—Semi-upright, stoloniferous.

*Height and spread*.—Reaches about 60 cm in width and 35 cm in height.

*Cold hardiness*.—At least in U.S.D.A. Zone 4.

*Diseases and pest resistance*.—No susceptibility or resistance to diseases or pests has been observed.

*Environmental tolerances*.—Low to moderate rain tolerance, moderate to high wind tolerance.

*Root description*.—Fibrous.

*Propagation*.—Stem cuttings and tissue culture.

*Root development*.—Roots initiate in about 2 weeks and a young fully rooted plant is produced in 4 to 5 months.

*Growth rate*.—Moderate.

*Stem description*.—Acaulescent, 4 basal rosettes present.

*Stolon description*.—An average of 79 cm in length and 3.5 mm in diameter, 144A to 144B in color and sparsely covered with soft thin hairs; 1.5 mm in length, transparent and NN155D in color.

Foliage description:

*Leaf division*.—Compound, 3 leaflets.

*Leaf arrangement*.—Basal rosettes.

*Leaf shape*.—Reniform.

*Leaf attachment*.—Petiolate.

*Leaf size*.—An average of 20 cm in length and 11.6 cm in width.

*Leaflet shape*.—Broadly obovate to nearly orbicular.

*Leaflet size*.—Average of 11.4 cm in length and 11.6 cm in width.

*Leaflet margins*.—Coarsely serrate-crenate.

*Angle of terminal leaflet to petiole*.—35° from vertical.

*Leaflet base*.—Broadly attenuate.

*Leaflet apex*.—Very short abruptly acute.

*Leaflet profile*.—Slightly cupped downwards.

*Leaflet interveinal blistering*.—Moderately strong.

*Leaflet venation*.—Pinnate, upper surface; N144C, lower surface; 145B.

*Leaflet surface*.—Upper surface; satiny and sparsely pubescent with soft thin hairs; 1 mm in length, transparent and NN155D in color, lower surface; matte with main veins and secondary veins moderately to densely covered with very thin soft adpressed hairs; 1 mm in length, transparent, and NN155D in color, both surfaces rugose.

*Leaflet color*.—Upper surface; young N144C and 143B near margins, mature 137A, lower surface; young 144B, mature a color between 138B and 191A.

*Petiole*.—Round in shape, 144B in color, average of 32 cm in length and 4 mm in diameter, surface densely covered with thin soft strigose hairs; 2 mm in length, transparent and NN155D in color.

*Petiolules*.—None or very short, 44B in color, round in shape, average of 2 mm in length and 1.5 mm in width, surface densely covered with thin soft strigose hairs; 2 mm in length, transparent and NN155D in color.

*Stipules*.—

Flower description:

*Blooming period*.—About 4 weeks in early to mid-summer in The Netherlands.

*Inflorescence*.—Compound cymose panicle.

*Inflorescence size*.—Average of 7.1 cm (excluding peduncle) in length and 6.8 cm in diameter.

*Number of flowers per inflorescence*.—Average of 5 (occasionally 6).

*Flower buds*.—Broad ovate to nearly orbicular in shape, an average of 1.2 cm in length and diameter, color 146D with base N144D and immature petal portion 157D, surface matte and moderately covered with soft thin hairs; 1 mm in length, transparent, and 157D in color.

*Flower type*.—Rotate, single.

*Flower aspect*.—Outward to upright.

*Flower fragrance*.—Moderate in strength and sweet.

*Flower size*.—Average of 3.2 cm in height and diameter.

*Flower longevity*.—An average of one week, self-cleaning.

*Calyx*.—Rotate, held slightly upright, an average of 3.5 cm in diameter and 3 mm in height.

*Sepals*.—Lanceolate, an average of 10 (5 longer and 5 shorter), longer sepals an average of 1.3 cm in length and 4 mm in width, shorter sepals an average of 9 mm in length and 4 mm in width, color longer sepals; upper surface when opening 143A, when mature 137C with tip 143A, lower surface when opening 143B, when mature 143B, when mature 137C with tip 143A, color of shorter sepals; upper surface when opening 144C with tip 143A, when mature 145B with tip 144A, lower surface when opening 144B, when mature 145A, surface upper surface sparsely covered with thin soft hairs; 1 mm in length and NN155D in color, surface lower surface sparsely covered with thin soft hairs; 1 mm in length and 157D in color, base broadly cuneate and fused, acute apex.

*Petals*.—Average of 5, average of 1.3 cm in length and 1.25 cm in width, not touching to slightly overlapping, margin entire, apex obtuse, base cuneate, slightly undulated, color NN155D on upper and lower surface when opening, color when mature upper surface NN155D, color lower when mature NN155C, surface glabrous, smooth, and moderately velvety.

*Peduncle*.—144C in color, an average of 22 cm in length and 4 mm in diameter, surface slightly glossy and densely covered with thin soft hairs; 2 mm in length and NN155D and 157D in color, held at an average angle of 50° to horizontal.

*Pedicel*.—144C in color, an average of 2 cm in length and 1.5 mm in diameter, surface densely covered with thin soft hairs; 1 mm in length and NN155D in color, held at an average angle of 45° to peduncle.

*Bracts*.—2 at the base of each pedicel, narrow elliptic to narrow ovate in shape, carinate, apex narrow acuminate, base attenuate, an average of 2.2 cm in length and 5 mm in width, color upper surface 143A and lower surface 138B, surface upper surface glabrous, lower surface densely covered with thin soft adpressed hairs; 1 mm in length, transparent, and 157D in color.

*Pistils*.—Average of 120, average of 1 mm in length, stigma club-shaped, 0.3 mm in length and width, 153D in color, style 0.9 mm in length, 1A and 1B in color.

*Stamens*.—Average of 25, filaments 4 mm in length and 145D in color, anthers 1 mm in length, and 0.75 mm in width, 153D in color, pollen low in quantity and 13B to 13C in color.

Fruit description:

*Shape*.—Conic.

*Surface*.—Smooth, glassy, pistil styles persistent; average of 0.75 mm in length, and 200C in color.

*Calyx position*.—Even to slightly impressed.

*Diameter of calyx relative to fruit diameter*.—Similar.

*Adherence of calyx*.—Strong.

*Glossiness*.—Even.

*External color* (*skin*).—158A and 161D with sunny side tinged with 35A to 34B and 42D.

*Internal color*.—NN155A with margins towards sunny side slightly tinged with 34A.

*Evenness of color of skin*.—Varies with sunny expose.

*Evenness of color of flesh*.—Even but tinged towards margin on sun exposed side.

*Fruit sweetness/taste*.—Sweet, slightly acidic taste.

*Fruit firmness*.—Very firm.

*Fruit weight*.—10 to 20 grams.

*Fruit quantity*.—Average of 22.

*Fruit size*.—Average of 3.5 cm in length and diameter.

*Season of harvest*.—June bearing in The Netherlands.

*Achenes*.—Color 34A when mature, 1.25 mm in length and 0.8 mm in diameter, smooth and glabrous surface, average of 120, deeply inserted.

*Longevity of fruit*.—An average of 1 week after harvest.

It is claimed:

1. A new and distinct cultivar of *Fragaria* plant named 'Blossomberry' as herein illustrated and described.

* * * * *